(12) United States Patent
Marecki et al.

(10) Patent No.: US 11,622,764 B2
(45) Date of Patent: Apr. 11, 2023

(54) SURGICAL HANDLE ASSEMBLY

(71) Applicant: Lexington Medical, Inc., Billerica, MA (US)

(72) Inventors: Andrew Marecki, West Boylston, MA (US); Richard Moyer, Allston, MA (US)

(73) Assignee: Lexington Medical, Inc., Bedford, MA (US)

( * ) Notice: Subject to any disclaimer, the term of this patent is extended or adjusted under 35 U.S.C. 154(b) by 50 days.

(21) Appl. No.: 17/241,538

(22) Filed: Apr. 27, 2021

(65) Prior Publication Data
US 2022/0338874 A1    Oct. 27, 2022

(51) Int. Cl.
*A61B 17/072* (2006.01)
*A61B 17/29* (2006.01)
*A61B 17/00* (2006.01)

(52) U.S. Cl.
CPC .......... *A61B 17/07207* (2013.01); *A61B 2017/00398* (2013.01); *A61B 2017/07271* (2013.01); *A61B 2017/07285* (2013.01); *A61B 2017/2925* (2013.01); *A61B 2017/2943* (2013.01)

(58) Field of Classification Search
CPC .... A61B 17/07207; A61B 2017/00398; A61B 2017/07271; A61B 2017/07285; A61B 2017/2925; A61B 2017/2943
USPC ...................................... 227/180.1
See application file for complete search history.

(56) References Cited

U.S. PATENT DOCUMENTS

| | | |
|---|---|---|
| 4,737,608 A | 4/1988 | Jones |
| 4,978,049 A | 12/1990 | Green |
| 5,300,081 A | 4/1994 | Young et al. |
| 5,326,013 A | 7/1994 | Green et al. |
| RE34,680 E | 8/1994 | Lieser |
| 5,474,223 A | 12/1995 | Viola et al. |
| 5,489,058 A | 2/1996 | Plyley et al. |
| 5,489,292 A | 2/1996 | Tovey et al. |
| 5,507,426 A | 4/1996 | Young et al. |
| 5,522,534 A | 6/1996 | Viola et al. |
| 5,535,935 A | 7/1996 | Vidal et al. |
| 5,586,711 A | 12/1996 | Plyley et al. |
| 5,588,579 A | 12/1996 | Schnut et al. |
| 5,758,814 A | 6/1998 | Gallagher et al. |
| 5,762,256 A | 6/1998 | Mastri et al. |
| 5,799,857 A | 9/1998 | Robertson et al. |
| 5,823,066 A | 10/1998 | Huitema |
| 5,836,503 A | 11/1998 | Ehrenfels et al. |
| 5,865,361 A | 2/1999 | Milliman et al. |

(Continued)

FOREIGN PATENT DOCUMENTS

| | | |
|---|---|---|
| EP | 1563791 | 8/2005 |
| EP | 1563792 | 8/2005 |

(Continued)

*Primary Examiner* — Dariush Seif
(74) *Attorney, Agent, or Firm* — Brooks, Cameron & Huebsch, PLLC

(57) ABSTRACT

The present disclosure includes apparatuses for a surgical handle assembly. An example apparatus includes a reloadable cartridge assembly and a surgical handle assembly including a spring positioned in the surgical handle assembly at a proximal end of a toothed rack. Proximal movement of the toothed rack causes the spring to be compressed and allows for complete opening of the reloadable cartridge assembly.

20 Claims, 5 Drawing Sheets

DETAIL C

(56) References Cited

U.S. PATENT DOCUMENTS

| | | | |
|---|---|---|---|
| 5,901,895 A | 5/1999 | Heaton et al. |
| 6,109,500 A | 8/2000 | Alli et al. |
| 6,281,453 B1 | 8/2001 | Uleski |
| 6,302,798 B1 | 10/2001 | Nakaguro |
| 6,945,444 B2 | 9/2005 | Gresham et al. |
| 6,957,758 B2 | 10/2005 | Aranyi |
| 7,044,352 B2 | 5/2006 | Shelton, IV et al. |
| 7,044,353 B2 | 5/2006 | Mastri et al. |
| 7,097,089 B2 | 8/2006 | Marczyk |
| 7,143,923 B2 | 12/2006 | Shelton, IV et al. |
| 7,143,924 B2 | 12/2006 | Scirica et al. |
| 7,168,604 B2 | 1/2007 | Milliman et al. |
| 7,225,963 B2 | 6/2007 | Scirica |
| 7,234,624 B2 | 6/2007 | Gresham et al. |
| 7,303,106 B2 | 12/2007 | Milliman et al. |
| 7,325,713 B2 | 2/2008 | Aranyi |
| 7,364,060 B2 | 4/2008 | Milliman |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,404,508 B2 | 7/2008 | Smith et al. |
| RE40,514 E * | 9/2008 | Mastri ............... A61B 17/072 227/176.1 |
| 7,422,136 B1 | 9/2008 | Marczyk |
| 7,455,208 B2 | 11/2008 | Wales et al. |
| 7,490,749 B2 | 2/2009 | Schall et al. |
| 7,494,038 B2 | 2/2009 | Milliman |
| 7,516,877 B2 | 4/2009 | Aranyi |
| 7,546,940 B2 | 6/2009 | Milliman et al. |
| 7,611,038 B2 | 11/2009 | Racenet et al. |
| 7,624,902 B2 | 12/2009 | Marczyk et al. |
| 7,694,865 B2 | 4/2010 | Scirica |
| 7,780,055 B2 | 8/2010 | Scirica et al. |
| 7,802,712 B2 | 9/2010 | Milliman et al. |
| 7,832,408 B2 | 11/2010 | Shelton, IV et al. |
| 7,837,079 B2 | 11/2010 | Holsten et al. |
| 7,845,535 B2 | 12/2010 | Scircia |
| 7,857,187 B2 | 12/2010 | Milliman |
| 7,926,692 B2 | 4/2011 | Racenet et al. |
| 7,963,431 B2 | 6/2011 | Scirica |
| 7,967,178 B2 * | 6/2011 | Scirica ............... A61B 17/0682 227/19 |
| 7,967,180 B2 | 6/2011 | Scirica |
| 8,020,743 B2 | 9/2011 | Shelton, IV |
| 8,061,576 B2 | 11/2011 | Cappola |
| 8,070,036 B1 | 12/2011 | Knodel |
| 8,123,101 B2 | 2/2012 | Racenet et al. |
| 8,136,712 B2 | 3/2012 | Zingman |
| 8,141,763 B2 | 3/2012 | Milliman |
| 8,157,148 B2 | 4/2012 | Scirica |
| 8,235,274 B2 | 8/2012 | Cappola |
| 8,292,157 B2 | 10/2012 | Smith et al. |
| 8,328,822 B2 | 12/2012 | Huitema et al. |
| 8,336,751 B2 | 12/2012 | Scirica |
| 8,336,754 B2 | 12/2012 | Cappola et al. |
| 8,342,378 B2 | 1/2013 | Marczyk |
| 8,360,296 B2 | 1/2013 | Zingman |
| 8,413,868 B2 | 4/2013 | Cappola |
| 8,424,736 B2 | 4/2013 | Scirica et al. |
| 8,573,460 B2 | 11/2013 | Cappola |
| 8,573,463 B2 | 11/2013 | Scirica |
| 8,608,043 B2 | 12/2013 | Scirica |
| 8,622,894 B2 | 1/2014 | Banik et al. |
| 8,684,247 B2 | 4/2014 | Scirica et al. |
| 8,684,249 B2 | 4/2014 | Racenet et al. |
| 8,695,865 B2 | 4/2014 | Smith et al. |
| 8,888,814 B2 | 11/2014 | Cappola |
| 8,910,847 B2 | 12/2014 | Nalagatla et al. |
| 9,204,876 B2 | 12/2015 | Cappola et al. |
| 9,364,218 B2 | 6/2016 | Scirica |
| 9,393,016 B2 | 7/2016 | Scirica et al. |
| 9,522,029 B2 * | 12/2016 | Yates ............... A61B 90/98 |
| 9,539,006 B2 | 1/2017 | Collings et al. |
| 9,655,617 B2 | 5/2017 | Cappola |
| 9,861,358 B2 | 1/2018 | Marczyk et al. |
| 9,931,739 B2 | 4/2018 | Nelson |
| 10,383,634 B2 | 8/2019 | Shelton, IV |
| 2005/0006429 A1 | 1/2005 | Wales |
| 2006/0111210 A1 | 5/2006 | Hinman |
| 2007/0125826 A1 | 6/2007 | Shelton, IV |
| 2007/0262116 A1 | 11/2007 | Hueil et al. |
| 2008/0083810 A1 | 4/2008 | Marczyk |
| 2008/0179374 A1 | 7/2008 | Beardsley et al. |
| 2009/0062614 A1 | 3/2009 | Adzich et al. |
| 2009/0145947 A1 | 6/2009 | Scirica et al. |
| 2009/0272614 A1 | 11/2009 | Watarai |
| 2010/0264193 A1 | 10/2010 | Huang et al. |
| 2011/0062211 A1 | 3/2011 | Ross |
| 2011/0253765 A1 | 10/2011 | Nicholas |
| 2012/0116391 A1 * | 5/2012 | Houser ............... A61B 34/76 606/1 |
| 2012/0286019 A1 | 11/2012 | Hueil |
| 2013/0053831 A1 * | 2/2013 | Johnson ............... A61B 18/085 606/1 |
| 2013/0092719 A1 | 4/2013 | Kostrzewski |
| 2013/0199327 A1 | 8/2013 | Park et al. |
| 2013/0245676 A1 | 9/2013 | Cappola |
| 2013/0304115 A1 | 11/2013 | Miyamoto |
| 2015/0196996 A1 | 7/2015 | Nelson |
| 2015/0342605 A1 | 12/2015 | Abbott et al. |
| 2015/0374396 A1 | 12/2015 | Strobl |
| 2016/0074106 A1 * | 3/2016 | Garrison ............... A61B 17/29 606/41 |
| 2016/0089175 A1 * | 3/2016 | Hibner ............... A61B 17/282 606/205 |
| 2016/0166250 A1 | 6/2016 | Marczyk |
| 2016/0270786 A1 | 9/2016 | Scirica |
| 2017/0000485 A1 | 1/2017 | Shelton, IV et al. |
| 2017/0172577 A1 | 6/2017 | Wenchell et al. |
| 2017/0252096 A1 * | 9/2017 | Felder ............... A61B 17/32 |
| 2017/0281177 A1 | 10/2017 | Harris et al. |
| 2017/0281184 A1 | 10/2017 | Shelton, IV |
| 2017/0281220 A1 | 10/2017 | Hibner |
| 2018/0021041 A1 * | 1/2018 | Zhang ............... A61B 17/1155 227/175.2 |
| 2018/0078354 A1 | 3/2018 | Cardinale et al. |
| 2018/0168599 A1 | 6/2018 | Bakos |
| 2018/0289370 A1 | 10/2018 | Amariglio et al. |
| 2018/0310935 A1 | 11/2018 | Wixey |
| 2018/0317915 A1 | 11/2018 | McDonald, II |
| 2018/0368832 A1 | 12/2018 | Marecki et al. |
| 2019/0261984 A1 * | 8/2019 | Nelson ............... A61B 17/07207 |
| 2019/0290265 A1 * | 9/2019 | Shelton, IV ....... H02J 7/007186 |
| 2020/0008801 A1 | 1/2020 | Somekh et al. |
| 2020/0015818 A1 | 1/2020 | Amariglio et al. |
| 2020/0093486 A1 | 3/2020 | Somekh et al. |
| 2020/0222046 A1 * | 7/2020 | Somekh ............... A61B 17/07207 |
| 2021/0007740 A1 | 1/2021 | Marecki et al. |

FOREIGN PATENT DOCUMENTS

| | | |
|---|---|---|
| EP | 1563794 | 8/2005 |
| EP | 1709911 | 10/2006 |
| EP | 1021130 | 11/2006 |
| EP | 2253277 | 11/2010 |
| EP | 2253278 | 11/2010 |
| EP | 2886020 | 6/2015 |
| EP | 2484290 | 7/2015 |
| EP | 2311385 | 5/2017 |

* cited by examiner

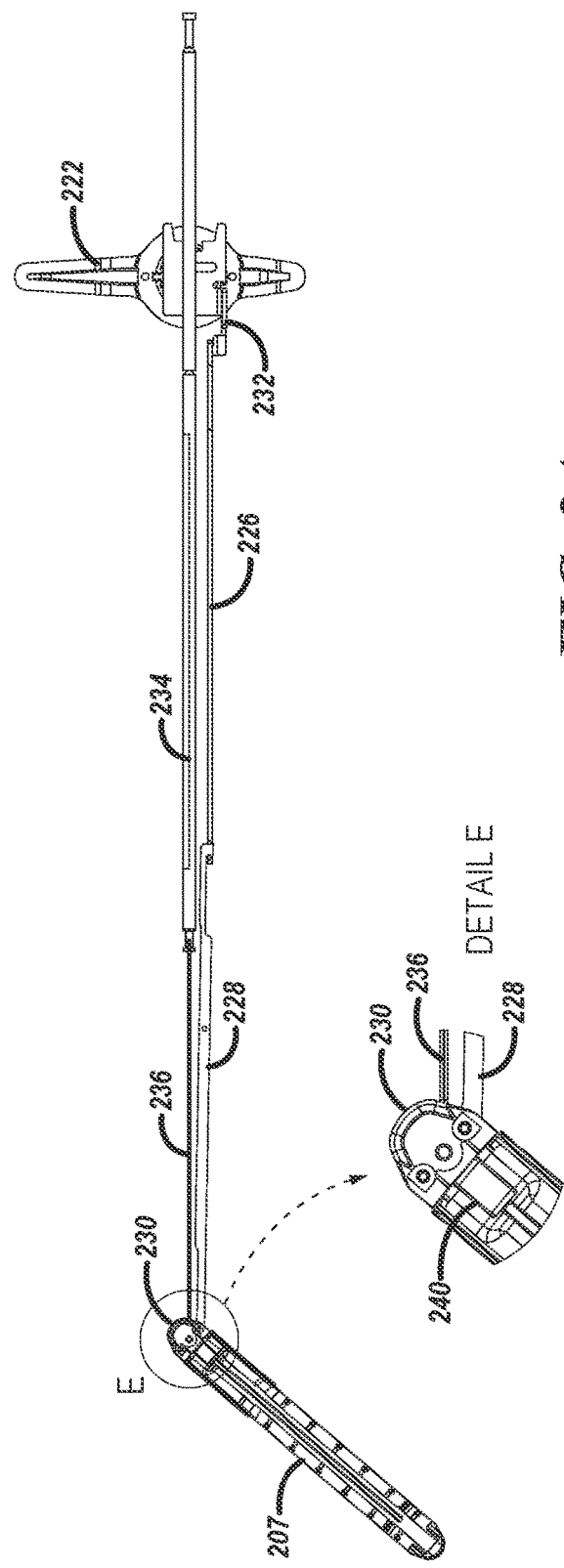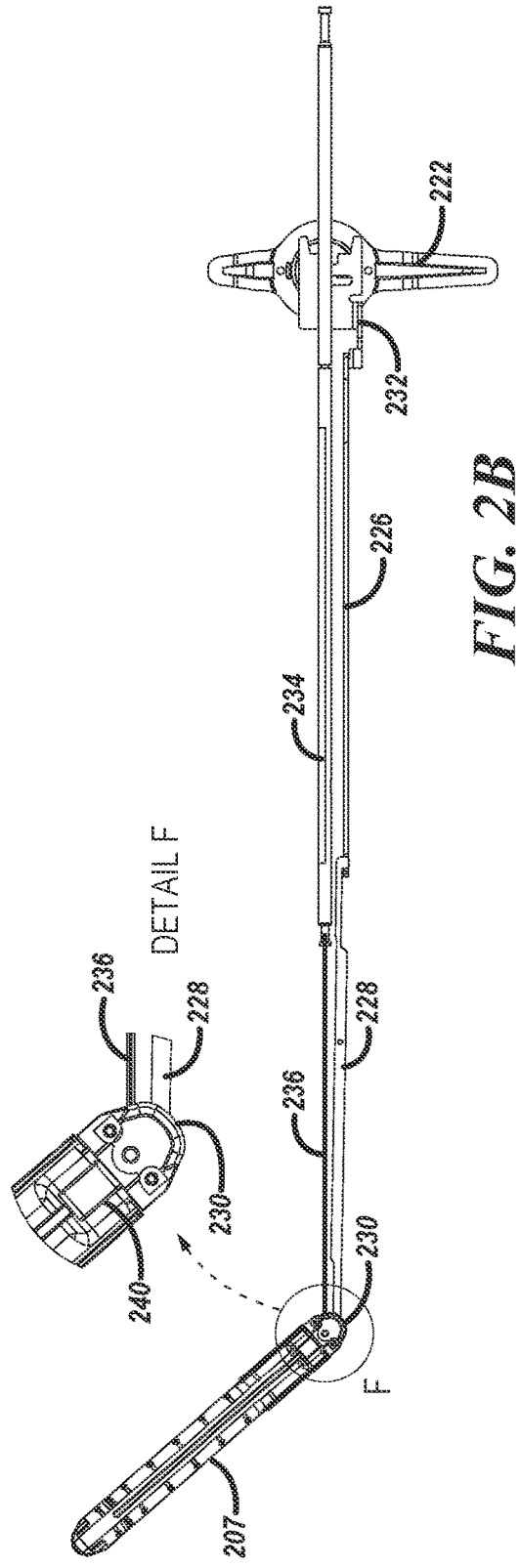
FIG. 2A
FIG. 2B

DETAIL C

SURGICAL HANDLE ASSEMBLY

TECHNICAL FIELD

The present disclosure relates generally to an articulatable surgical handle assembly.

BACKGROUND

A surgical handle assembly can be used in a number of surgical devices. One example includes use as a surgical stapler. A surgical stapler is a fastening device used to clamp tissue between opposing jaw structures to join tissue using surgical fasteners. Surgical staplers can include two elongated members used to clamp the tissue. One of the elongated members can include one or more reloadable cartridges and the other elongated member can include an anvil that can be used to form a staple when driven from the reloadable cartridge. A surgical stapler can receive one or more reloadable cartridges. An example of reloadable cartridges can include having rows of staples having a linear length. For example, a row of staples can have a linear length between 30 mm and 60 mm. A staple can be ejected by actuation of a movable handle member that is a part of the surgical handle assembly of the surgical stapler.

Some surgical staplers are equipped with an articulation mechanism that causes the distal portion of the stapler, the elongated members or jaws which house a staple cartridge and an anvil for forming the staples, to move away from or toward the longitudinal axis of the stapler. Articulation is an important feature of a stapler as it allows a physician or other user of the stapler to properly position the stapler jaws in the proper location and orientation. Some staplers also have a feature that allow a physician to open and close the jaws multiple times prior to delivering the staples. In some staplers that are equipped with an articulation arm, when the jaws of the stapler are articulated, the design of the stapler assembly will not allow the jaws to return to a fully open position.

BRIEF DESCRIPTION OF THE DRAWINGS

FIG. 2A is a schematic diagram of an apparatus including an articulation assembly and a drive assembly in accordance with a number of embodiments of the present disclosure.

FIG. 2B is a schematic diagram of an apparatus including an articulation assembly and a drive assembly in accordance with a number of embodiments of the present disclosure.

DETAILED DESCRIPTION

Figure 1:
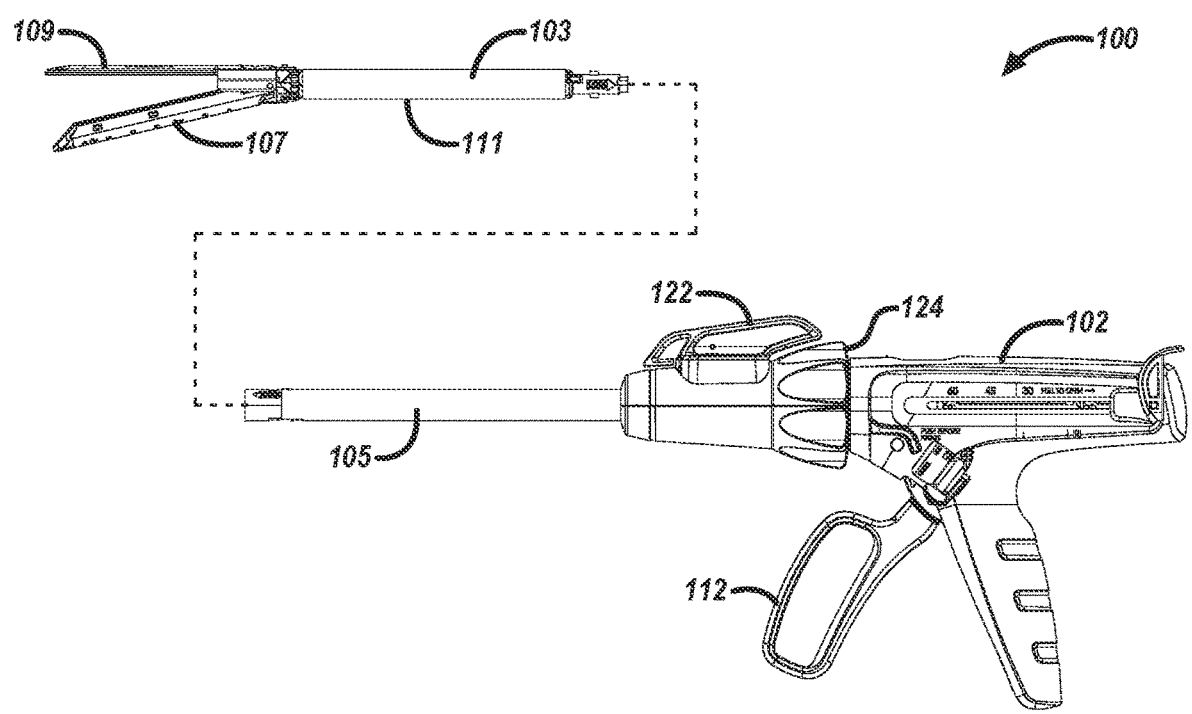
FIG. 1 is a schematic diagram of an apparatus including a surgical handle assembly and a reloadable cartridge assembly in accordance with a number of embodiments of the present disclosure.

The present disclosure includes apparatuses for a surgical handle assembly and surgical handles. An example apparatus includes a reloadable cartridge assembly and a surgical handle assembly including an articulation assembly configured to maintain the reloadable cartridge assembly in various positions. In some surgical handle reloadable cartridge assemblies, the user can articulate the distal end of the assembly by rotating a knob and cam assembly. Rotation of the knob and cam assembly causes an articulation arm to move in a linear direction.

In a number of embodiments, the reloadable cartridge assembly can include a first elongated member and a second elongated member that can be used to clamp tissue. One of the elongated members can house one or more staple cartridges. The other elongated member can have an anvil that can be used to form a staple when driven from the staple cartridge. Some reloadable cartridge assemblies have rows of staples. When in use and connected to a surgical handle assembly, a physician may rotate a knob and cam assembly of an articulation assembly. Rotation of the knob and cam assembly causes the articulation arm of the surgical handle assembly to move in a linear direction and, since the handle assembly is connected to the cartridge assembly, the articulation arm of the cartridge assembly will correspondingly move in a linear direction. This linear movement causes the elongated members to move away from or toward the longitudinal axis of the reloadable cartridge assembly.

Many surgical handle assemblies comprise a toothed rack that interacts with a movable handle and can move proximally and distally. A drive shaft can be connected to a distal end of the toothed rack and, when the reloadable cartridge assembly is attached to the surgical handle assembly, the drive shaft is connected to a blade shaft in the reloadable cartridge assembly. Distal movement of the toothed rack will cause open elongated members to close or clamp. Further distal movement of the toothed rack will cause staples to be delivered. If, at the point when the elongated members have just closed, the toothed rack is moved proximally, the elongated members will reopen or unclamp.

When articulated, the design of some prior art reloadable cartridge assemblies and/or surgical handle assemblies will not allow the elongated members to fully open during the unclamp process. Embodiments of this disclosure include surgical handle assembly designs that allow the elongated members to fully open even when the elongated members are in an articulated position.

In the following detailed description of the present disclosure, reference is made to the accompanying drawings that form a part hereof, and in which is shown by way of illustration how one or more embodiments of the disclosure may be practiced. These embodiments are described in sufficient detail to enable those of ordinary skill in the art to practice the embodiments of this disclosure, and it is to be understood that other embodiments may be utilized and that process, electrical, and structural changes may be made without departing from the scope of the present disclosure.

It is to be understood that the terminology used herein is for the purpose of describing particular embodiments only and is not intended to be limiting. As used herein, the singular forms "a", "an", and "the" can include both singular and plural referents, unless the context clearly dictates otherwise. In addition, "a number of", "at least one", and "one or more" can refer to one or more things, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to". The terms "coupled"

and "coupling" mean to be directly or indirectly connected physically or for access to and movement of the movable handle member, as appropriate to the context.

The figures herein follow a numbering convention in which the first digit or digits correspond to the figure number and the remaining digits identify an element or component in the figure. Similar elements or components between different figures may be identified by the use of similar digits. For example, 448 may reference element "48" in FIG. 4, and a similar element may be referenced as 548 in FIG. 5. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a schematic diagram of an apparatus 100 including a surgical handle assembly 102 and a reloadable cartridge assembly 103 in accordance with a number of embodiments of the present disclosure. In some embodiments, the apparatus 100 can be a surgical stapler, for example.

As shown in the example of FIG. 1, the reloadable cartridge assembly 103, e.g. a disposable loading unit, can be releasably secured to a distal end of an elongated body of the surgical handle assembly 102. In this example, the reloadable cartridge assembly 103 can include a cartridge shaft 111 and a first elongated member 107 and a second elongated member 109 that can be used to clamp tissue. One of the elongated members can house one or more staple cartridges. The other elongated member can have an anvil that can be used to form a staple when driven from the staple cartridge. As mentioned, an apparatus 100 can receive reloadable cartridge assemblies having rows of staples. In a number of embodiments, third party reloadable cartridge and/or reloadable cartridge assemblies may be used with the surgical handle assembly 102 and embodiments of surgical handle assembly 102 may be configured to receive the same.

Handle assembly 102 can include a movable handle 112, radial positioner 124, knob and cam assembly 122 and handle shaft 105. The reloadable cartridge assembly 103 can be actuated using knob and cam assembly 122 and/or radial positioner 124. Radial positioner 124 rotates the reloadable cartridge assembly 103. Knob and cam assembly 122 positions the distal end of the reloadable cartridge assembly 103 at a particular angle for stapling. The knob and cam assembly 122 can be configured to actuate rotationally and the first elongated member 107 and the second elongated member 109 can rotate about an axis of a particular plane in response to the knob and cam assembly 122 being actuated rotationally by a user.

FIGS. 2A and 2B are schematic diagrams of an apparatus including an articulation assembly and a drive assembly in accordance with a number of embodiments of the present disclosure. With reference to FIG. 1, FIGS. 2A and 2B are views from the bottom of apparatus 100. All directional references for these figures will be with regard to the orientation shown in FIG. 1. The articulation assembly can include a knob and cam assembly 222, a cam connector 232, a handle articulation arm 226, and a reload articulation arm 228. Reload articulation arm 228 is connected to jaw pivot assembly 230. When a user rotates knob and cam assembly 222 to the left and/or counterclockwise, as illustrated in FIG. 2A, it causes cam connector 232 to move in a proximal direction which in turn pulls handle articulation arm 226 and reload articulation arm 228 proximally. This causes the elongated members (e.g., elongated members 107 and 109 in FIG. 1) to move toward the left and/or counterclockwise. When a user rotates knob and cam assembly 222 to the right and/or clockwise, as illustrated in FIG. 2B, it causes cam connector 232 to move in a distal direction which in turn pushes the handle articulation arm 226 and the reload articulation arm 228 distally. This causes the elongated members to move toward the right and/or clockwise.

FIGS. 2A and 2B also show a drive mechanism for an apparatus, for example, a surgical stapler. The drive mechanism can include a toothed rack (e.g., toothed rack 340, 440, and 540 in FIGS. 3, 4, and 5, respectively), a drive shaft 234, and a blade shaft 236. As will be explained later, movement of a movable handle (e.g., movable handle 112 in FIG. 1) can cause distal and proximal movement of the toothed rack. This movement is transferred through drive shaft 234 and blade shaft 236 to I-beam 240. Distal movement of the toothed rack can cause the elongated members to close or clamp. Proximal movement of the toothed rack can cause the elongated members to open or unclamp. When in the clamped position, further distal movement of the toothed rack can cause staples to be delivered.

The reload articulation arm 228 can be attached to the jaw pivot assembly 230 on the right side. When the jaw pivot assembly 230 is articulated toward the side of the reload articulation arm 228, to the right and/or clockwise as illustrated in FIG. 2A, the opening and/or unclamping of the elongated members is impaired as the pulling of articulation member 228 compresses a reloadable cartridge unit (e.g., reloadable cartridge unit 103 in FIG. 1) and the rest of the apparatus. This binding of the apparatus will not allow the elongated members to completely unclamp. Prior art apparatuses including surgical staplers may completely unclamp when in the straight, non-articulated position and on some occasions when articulated away from the side of the reload articulation arm 228. In some embodiments, completely unclamped means that the elongated members open to an angle greater than 8 degrees and not completely unclamped means that the elongated members will only open to an angle of 8 degrees or less.

In some embodiments, the knob and cam assembly 222, the cam connector 232, the handle articulation arm 226, the toothed rack, and the drive shaft 234 are located within a surgical handle assembly (e.g., surgical handle assembly 102) and the reload articulation arm 228, the blade shaft 236, and I-beam 240 are located within a reloadable cartridge assembly (e.g., reloadable cartridge assembly 103 in FIG. 1).

Figure 3:
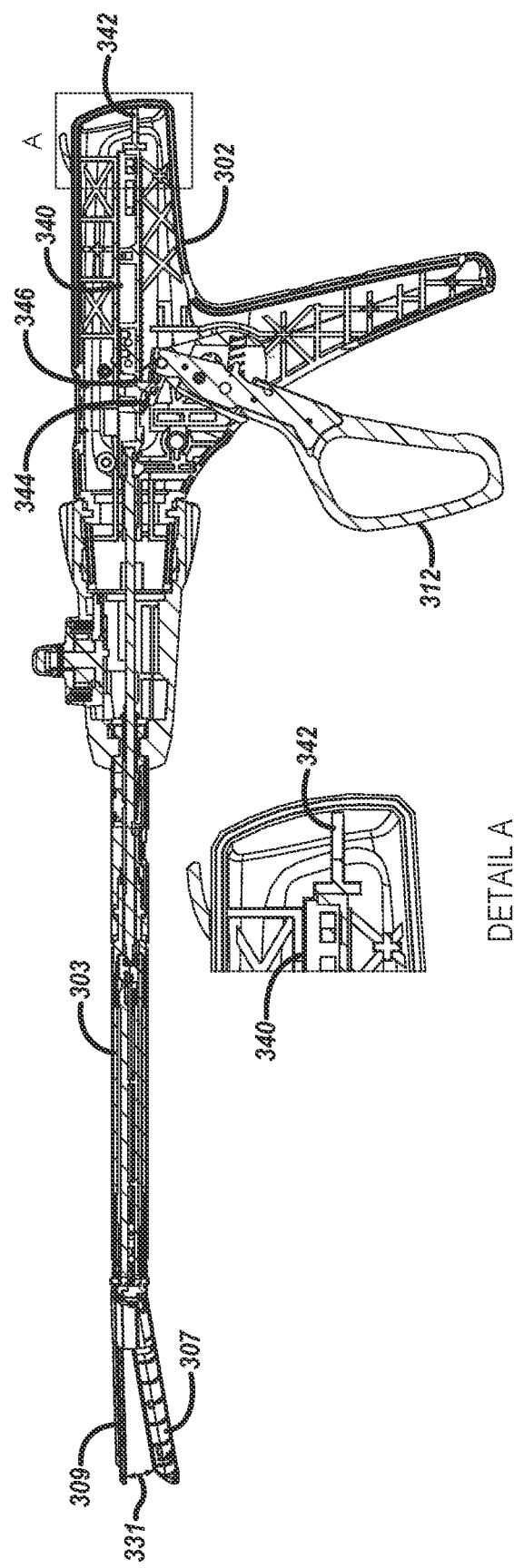
FIG. 3 is a schematic diagram of an apparatus including a prior art surgical handle assembly and a reloadable cartridge assembly in accordance with a number of embodiments of the present disclosure.

FIG. 3 is a schematic diagram of an apparatus including a prior art surgical handle assembly 302 and a reloadable cartridge assembly 303 in accordance with a number of embodiments of the present disclosure. Here, a stop 342 limits the proximal movement of toothed rack 340. It is important that the toothed rack 340 and/or the drive shaft (e.g., drive shaft 234 in FIGS. 2A and 2B) are properly positioned so that reloadable cartridges can be connected and/or disconnected. When the toothed rack 340 is in its most proximal position and is touching stop 342 the apparatus is in the loading position where reloadable cartridges can be connected and/or disconnected. Movement of movable handle 312 causes movement of driving pawl 344 and latch 346. During the clamping and unclamping process, proximal movement of the movable handle 312 causes driving pawl 344 to move in a distal direction which pushes toothed rack 340 in a distal direction. As discussed herein, this distal movement causes the I-beam (e.g., I-beam 240 in FIG. 2) of the reloadable cartridge assembly 303 to interact with elongated members 307 and 309 causing them to close and/or clamp. Distal movement of movable handle 312 causes latch 346 to interface with toothed rack 340 and to move toothed rack 340 in a proximal direction until the toothed rack 340 is at the loading position. This proximal movement of the toothed rack 340 causes the I-beam to move proximally allowing elongated members 307 and 309 to open and/or unclamp.

When the prior art apparatus of FIG. 3 is articulated, for example, towards a side of a reload articulation arm (e.g., reload articulation arm 228 in FIGS. 2A and 2B), the elongated members 307 and 309 of the prior art apparatus are prevented from completely opening and/or unclamping. For example, the prior art apparatus may only open to angle 331. Angle 331 can be 8 degrees or less. For example, the elongated members 307 and 309 can open to an angle 331 of 6 to 8 degrees.

Figure 4:
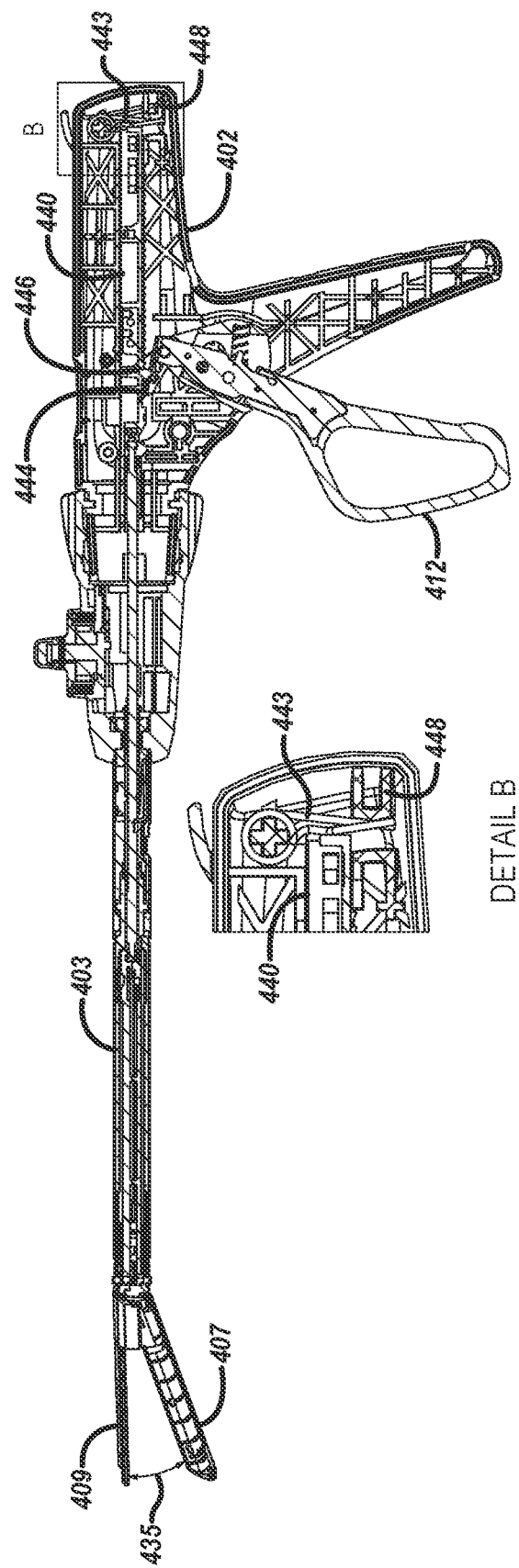
FIG. 4 is a schematic of diagram of an apparatus including a surgical handle assembly and a reloadable cartridge assembly in accordance with a number of embodiments of the present disclosure.

FIG. 4 is a schematic of diagram of an apparatus including a surgical handle assembly 402 and a reloadable cartridge assembly 403 in accordance with a number of embodiments of the present disclosure. FIG. 4 shows an aspect of the invention and is an instantaneous view of the movable handle 412 being moved distally during an unclamping process which causes latch 446 to move the toothed rack 440 in a proximal direction past a loading position. Additional movement of the blade shaft (e.g., blade shaft 236 in FIGS. 2A and 2B), drive shaft (e.g., drive shaft 234 in FIGS. 2A and 2B), and toothed rack 440 in the proximal direction causes the proximal end of toothed rack 440 to compress spring 443. This overshoot compensates for the play in the apparatus and allows the reload articulation arm (e.g., reload articulation arm 228 in FIGS. 2A and 2B) of the reloadable cartridge assembly 403 to be fully retracted and the elongated members 407 and 409 to fully open. This is a momentary position as the strength of the spring 443 will drive the toothed rack 440 distally back to the loading position. The spring 443 can have a force of 2 to 7 pounds. In a number of embodiments, the spring 443 can have a force of 18 Newtons or 4.05 pounds. In some examples, the spring 443 can have a force of between 4 and 5 pounds.

As illustrated in FIG. 4, the elongated members 407 and 409 may be fully open and/or unclamped when the proximal end of the toothed rack 440 is proximal of the loading position. Even when the elongated members 407 and 409 are articulated, for example, towards a side of an articulation arm (e.g., reload articulation arm 228 in FIGS. 2A and 2B), the elongated members 407 and 409 can completely open and/or unclamp. For example, the apparatus of FIG. 4 may open to angle 435. Angle 435 can be greater than angle 331 in FIG. 3. Angle 435 can be greater than 8 degrees. For example, the elongated members 407 and 409 can open to an angle 435 of 13 to 15 degrees.

In a number of embodiments, when positioning the apparatus (e.g., stapler) for use, either in open surgery or through an instrument such as a trocar, the clinician may need to rotate and/or articulate the elongated members 407 and 409 to position them properly. As the stapler is used to clamp, staple, and cut tissue, in some instances the clinician may need to clamp and unclamp the elongated members 407 and 409 to ensure that they are properly positioned. With some prior art devices, when the elongated members 407 and 409 are articulated, especially when the reload articulation arm is moved proximally, the stapler will bind up and the elongated members 407 and 409 will not be able to fully open. In this instance, the clinician either puts up with the non-optimal opening or can move the elongated members 407 and 409 to a non-articulated position to fully open them.

With the embodiments of this invention, when the clinician attempts to unclamp the elongated members 407 and 409, they will fully reopen allowing for easier and more accurate placement. Once the elongated members 407 and 409 are in position, the clinician will clamp the elongated members 407 and 409 and deliver the staples. The cutter on the I-beam (e.g., I-beam 240 in FIGS. 2A and 2B) will cut the tissue as the staples are being delivered.

Figure 5:
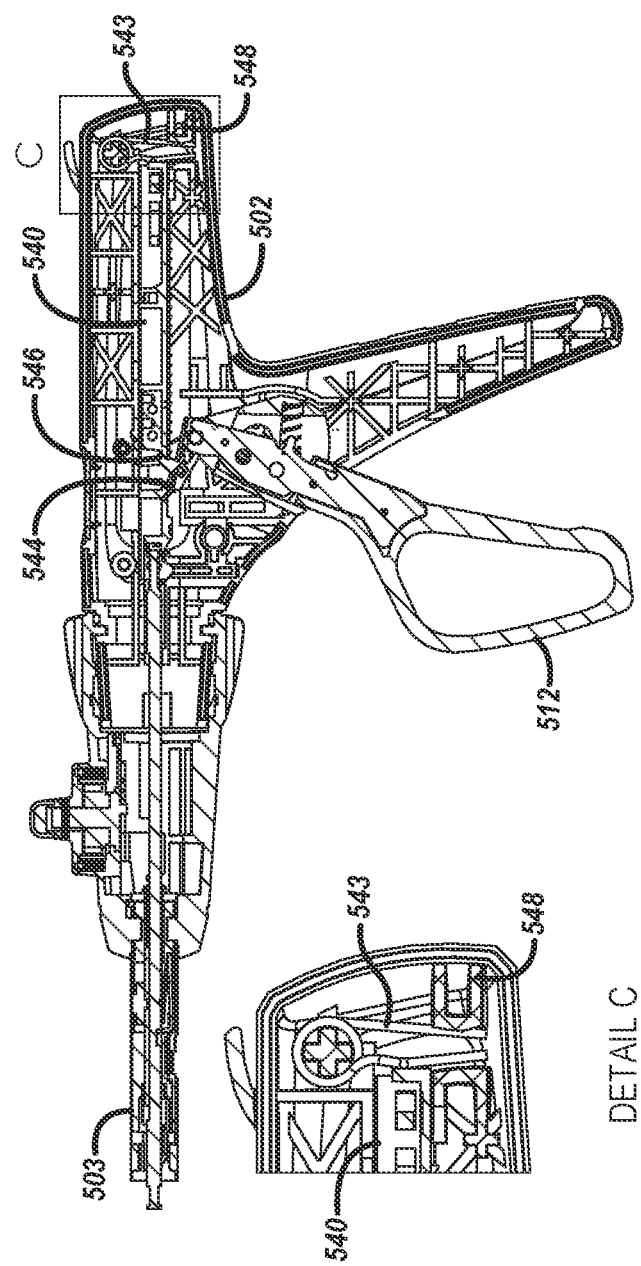
FIG. 5 is a schematic diagram of an apparatus including a surgical handle assembly in accordance with a number of embodiments of the present disclosure.

FIG. 5 is a schematic diagram of an apparatus including a surgical handle assembly 502 in accordance with a number of embodiments of the present disclosure. FIG. 5 illustrates the toothed rack 540 in the loading position. Here, a spring 543 is positioned at the proximal end of toothed rack 540. The spring 543 allows the toothed rack 540 to move proximally past the loading position before the spring 543 returns the toothed rack 540 to the loading position. After the movable handle 512 has been moved proximally and the distal movement of the toothed rack 540 causes elongated members (e.g., elongated members 407 and 409 in FIG. 4) to clamp, distal movement of the movable handle 512 can cause the latch 546 to drive the toothed rack 540 proximally. Further movement will cause the toothed rack 540 to overshoot the loading position. For example, a proximal end of the toothed rack 540 will be positioned proximal of the loading position. This overshoot allows for the unloading (or uncompressing) of a reloadable cartridge assembly (e.g., reloadable cartridge assembly 403 in FIG. 4). By allowing the toothed rack 540, drive shaft (e.g., drive shaft 234 in FIGS. 2A and 2B), and blade shaft (e.g., blade shaft 236 in FIGS. 2A and 2B) to move proximal of the loading position, the I-beam (e.g., I-beam 240 in FIGS. 2A and 2B) can be fully retracted from the elongated members, allowing the elongated members to fully open and/or unclamp.

In FIG. 5, spring 543 is shown as a U-spring, although any spring or spongy material can be used as long as the spring mechanism allows for the proximal overshoot and has enough strength to move the toothed rack 540 back to the loading position. For example, a compression coil spring can be used. In a number of embodiments, a stop 548 may be used to properly position the spring 543. When toothed rack 540 is at rest and the proximal end of the toothed rack 540 is touching the unloaded or at rest spring 543, the surgical handle assembly 502 is in the loading position.

Although the embodiments were described with respect to a specific drive assembly and articulation assembly, the embodiments described herein are equally applicable to other drive mechanisms and articulation mechanisms. As long as the drive assembly and articulation assembly are comprised of rods or beams that travel in the shafts of the reloadable cartridge assembly and the surgical handle assembly 502, these embodiments are applicable. Similarly, in FIGS. 2A and 2B a particular arrangement of connecting the blade shaft 236 and reload articulation arm 228 to jaw pivot assembly 230 is shown. The embodiments of this disclosure are applicable to other connection arrangements. Regardless of the connection arrangement, when the reload articulation arm is pulled in a proximal direction and the elongated members are articulated to the articulation arm side or position, the elongated members will not fully open but can be fully opened if the teachings of this disclosure are followed.

In some of the embodiments described herein, the drive mechanism is the movable handle 512. These embodiments are equally applicable to powered handles where an electric motor drives the toothed rack and/or drive assembly. In some embodiments, an electric motor is configured to move the drive assembly while a movable handle 512 is used to clamp and unclamp the elongated members.

Some of the embodiments described herein have a surgical handle assembly 502 with a reloadable cartridge unit. The embodiments herein are equally applicable to a staple system where the reloadable cartridge unit is just a staple cartridge that is loaded into one of the elongated members.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A surgical stapler handle apparatus, comprising:
    a toothed rack;
    an articulation assembly configured to actuate an articulation arm of a reloadable cartridge assembly from a first operation position to a second operation position;
    a movable handle configured to actuate the toothed rack; and
    a spring positioned at a proximal end of the toothed rack,
    wherein when the proximal end of the toothed rack is touching the spring and the spring is unloaded and at rest the proximal end of the toothed rack is in a loading position;
    wherein when the proximal end of the toothed rack moves distally from the loading position, the proximal end of the toothed rack is disengaged from the spring; and
    wherein, when the movable handle is moved in a distal direction and the toothed rack is moved in a proximal direction, the movement of the toothed rack will cause the proximal end of the toothed rack to move proximally past the loading position and to compress the spring and wherein the spring is biased to move the toothed rack distally in response to the toothed rack moving proximally past the loading position.

2. The apparatus of claim 1 further comprising a driving pawl and a latch connected to the movable handle, the driving pawl interacting with the toothed rack to effect distal movement of the toothed rack and the latch interacting with the toothed rack to effect proximal movement of the toothed rack.

3. The apparatus of claim 1 wherein, when the spring is at rest and the proximal end of the toothed rack is touching the spring, the proximal end of the toothed rack is positioned in a loading position; and
    wherein proximal movement of the toothed rack causes the proximal end of the toothed rack to move proximal of the loading position and to compress the spring.

4. The apparatus of claim 3 wherein a force of the spring causes the proximal end of the toothed rack to move distally back to the loading position.

5. The apparatus of claim 4 wherein the force of the spring is between four and five pounds.

6. The apparatus of claim 1 further comprising an electric motor connected to the toothed rack such that the electric motor provides distal and proximal movement of the toothed rack.

7. An apparatus, comprising:
    a reloadable cartridge assembly comprising: a blade shaft, an articulation arm, and two opposable elongated members;
    a surgical handle assembly comprising an articulation assembly configured to actuate the articulation arm of the reloadable cartridge assembly from a first operation position to a second operation position, a toothed rack, a movable handle configured to actuate the toothed rack, and a spring positioned at a proximal end of the toothed rack;
    wherein when the proximal end of the toothed rack is touching the spring and the spring is unloaded and at rest the proximal end of the toothed rack is in a loading position;
    wherein when the proximal end of the toothed rack moves distally from the loading position, the proximal end of the toothed rack is disengaged from the spring; and
    wherein, when the movable handle is moved in a distal direction and the toothed rack is moved in a proximal direction, the movement of the toothed rack will cause the proximal end of the toothed rack to move proximally past the loading position and to compress the spring and wherein the spring is biased to move the toothed rack distally in response to the toothed rack moving proximally past the loading position.

8. The apparatus of claim 7 wherein proximal movement of the movable handle causes the blade shaft to move distally which causes the elongated members to close and distal movement of the movable handle causes the blade shaft to move proximally which causes the elongate members to open.

9. The apparatus of claim 8 wherein when the toothed rack is positioned proximal of the loading position, a force of the spring causes the toothed rack to be moved distally back to the loading position.

10. The apparatus of claim 9 further comprising a jaw pivot assembly connected to the elongated members and the articulation arm wherein movement of the articulation arm causes the elongated members to pivot away from the longitudinal axis of the reloadable cartridge assembly and wherein the movement of the articulation arm causes the reloadable cartridge assembly to become bound such that the elongated members are unable to fully open.

11. The apparatus of claim 10 wherein proximal movement of the toothed rack past the loading position causes the reloadable cartridge assembly to unbind such that the elongated members are able to fully open.

12. The apparatus of claim 11 wherein when the reloadable cartridge assembly is not bound the elongate members can fully reopen.

13. The apparatus of claim 9 further comprising a jaw pivot assembly connected to the elongated members and the articulation arm wherein proximal movement of the articulation arm causes the elongated members to pivot to the side that the articulation arm is connected to the jaw pivot assembly and wherein the proximal movement of the articulation arm causes the reloadable cartridge assembly to become bound such that the elongated members are unable to fully open.

14. A surgical stapler apparatus, comprising:
a reloadable cartridge assembly comprising: an articulation arm and two opposable elongated members;
a surgical handle assembly comprising an articulation assembly configured to actuate the articulation arm of the reloadable cartridge assembly from a first operation position to a second operation position, a drive assembly comprising a toothed rack, a motor configured to actuate the toothed rack, a spring positioned at a proximal end of the toothed rack, wherein when a proximal end of the toothed rack is touching the spring and the spring is unloaded and at rest the toothed rack is in the loading position and wherein when the proximal end of the toothed rack moves distally from the loading position, the proximal end of the toothed rack is disengaged from the spring; and
wherein, when the motor is activated and the toothed rack is moved in a proximal direction, the movement of the toothed rack will cause the toothed rack to move proximally past the loading position and to compress the spring and wherein the spring is biased to move the toothed rack distally in response to the toothed rack moving proximally past the loading position.

15. The apparatus of claim 14 further comprising a jaw pivot assembly connected to the elongated members and the articulation arm wherein movement of the articulation arm causes the elongated members to pivot away from the longitudinal axis of the reloadable cartridge assembly and wherein the movement of the articulation arm causes the reloadable cartridge assembly to become bound such that the elongated members are unable to fully open.

16. The apparatus of claim 14 wherein the surgical handle assembly further comprises a movable handle wherein proximal movement of the movable handle causes the toothed rack drive assembly to move distally which causes the elongated members to close and distal movement of the drive assembly causes a blade shaft to move proximally which causes the elongated members to open.

17. The apparatus of claim 16 wherein proximal movement of the toothed rack causes the proximal end of the toothed rack to move proximal of the loading position and to compress the spring.

18. The apparatus of claim 17 wherein a force of the spring causes the toothed rack to be moved distally back to the loading position.

19. The apparatus of claim 14, wherein the spring is a U-spring.

20. The apparatus of claim 14, wherein the two opposable elongated members open to an angle of 13 to 15 degrees when the toothed rack is moved past the loading position.

* * * * *